United States Patent [19]
Leisinger et al.

[11] Patent Number: 5,617,648
[45] Date of Patent: Apr. 8, 1997

[54] DRYER MOUNTED IN A HOUSING

[75] Inventors: Roger Leisinger, Zurich; Florian Philipp, Bertschikon; Tarik Oelmez, Winterthur, all of Switzerland

[73] Assignee: Mettler-Toledo AG, Greifensee, Switzerland

[21] Appl. No.: 594,134

[22] Filed: Jan. 31, 1996

[30] Foreign Application Priority Data

Apr. 4, 1995 [CH] Switzerland .......................... 949959

[51] Int. Cl.$^6$ .................................................. F26B 19/00
[52] U.S. Cl. ............................. 34/226; 34/202; 34/308; 177/180; 177/245
[58] Field of Search ........................... 34/202, 226, 308, 34/536; 177/180, 200, 245

[56] References Cited

U.S. PATENT DOCUMENTS

| | | | |
|---|---|---|---|
| 4,465,152 | 8/1984 | Schmitter | 177/180 |
| 4,703,151 | 10/1987 | Sakamoto | 219/518 |
| 4,964,734 | 10/1990 | Yoshida et al. | 374/14 |
| 5,402,672 | 4/1995 | Bradford | 73/76 |
| 5,485,684 | 1/1996 | Phillip et al. | 34/226 |

*Primary Examiner*—Henry A. Bennett
*Assistant Examiner*—Dinnatia Doster
*Attorney, Agent, or Firm*—Friedrich Kueffner

[57] ABSTRACT

A dryer mounted in a housing includes a precision balance arranged in the housing for determining the moisture content of material to be weighed which is placed on a weighing dish and is subjected to heat radiation from a heat source of the dryer. For making the material to be weighed accessible, the precision balance can be moved in and out of the housing. A duct for conducting an air flow is mounted between the weighing dish and the load-receiving unit which supports the weighing dish and is mounted above the measuring cell of the precision balance.

8 Claims, 4 Drawing Sheets

DRYER MOUNTED IN A HOUSING

BACKGROUND OF THE INVENTION

1. Field of the Invention

The present invention relates to a dryer which is mounted in a housing. The dryer includes a precision balance arranged in the housing for determining the moisture content of material to be weighed which is placed on a weighing dish and is subjected to heat radiation from a heat source of the dryer. For making the material to be weighed accessible, the weighing dish can be moved in and out of the housing.

2. Description of the Related Art

A dryer with a precision balance mounted in the dryer for determining the moisture content of the material to be weighed is disclosed in prior application Ser. No. 08/163,925, now U.S. Pat. No. 5,485,684. The measuring cell of the precision balance with the weighing dish mounted thereon is constructed in such a way that it can be moved in and out of the housing for charging and weighing-in of the material to be weighed. In the moved-in state of the weighing dish, a heat source is mounted in the housing above the weighing dish, wherein the heat radiation of the heat source is transmitted directly from above onto the material to be weighed placed on the weighing dish. A cover glass for protecting the heat source against contamination may be mounted between the material to be weighed and the heat source.

When working with the known dryer, it is not possible to prevent the heat radiation of the heat source from not only heating the material to be weighed but also additional components which are within the range of radiation of the heat source. These components are particularly the weighing dish and the measuring cell of the precision balance as well as the protective cover glass between the heat source and the weighing dish. Errors of measurement may occur because of heating of the measuring cell due to the high temperatures.

SUMMARY OF THE INVENTION

Therefore, it is the primary object of the present invention to provide a dryer with precision balance of the above-described type in which the measuring cell is protected against being heated by the heat source which would influence the accuracy of the measuring cell.

In accordance with the present invention, means for conducting an air flow are mounted between the weighing dish and the load-receiving unit which supports the weighing dish and is mounted on the measuring cell of the precision balance.

The configuration according to the present invention makes it possible to thermally separate the hot area of the dryer with the heat source and the protective glass from the mechanical and electronic components of the balance. The separation not only takes place during drying, but also especially during the charging of the weighing dish and prevents heating of the weighing cell during charging of the moved-out balance. In the moved-out condition the weighing cell is directly underneath the heat source and underneath the protective glass which is heated by the heat source and continues to release heat radiation even when the heat source is switched off. Ambient air can be used for the thermal separation of the hot components from the measuring cell.

The means for conducting the air flow may be a duct which is closed to all sides in radial direction. The duct may be composed of two sections which are movable relative to each other. The sections which are movable relative to each other facilitate the thermal separation when the balance is in the moved-in position as well as during charging. In accordance with another feature of the present invention, it is ensured that flow of air through the duct takes place in any position of the balance. The two sections of the ducts can be connected to the housing of the dryer and to the balance, respectively, and are moved relative toward each other so that additional drive means for moving the sections relative to each other are not necessary. Thus, a continuous thermal separation of the hot and cold components of the dryer is ensured.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

DESCRIPTION OF THE PREFERRED EMBODIMENTS

Figure 1:
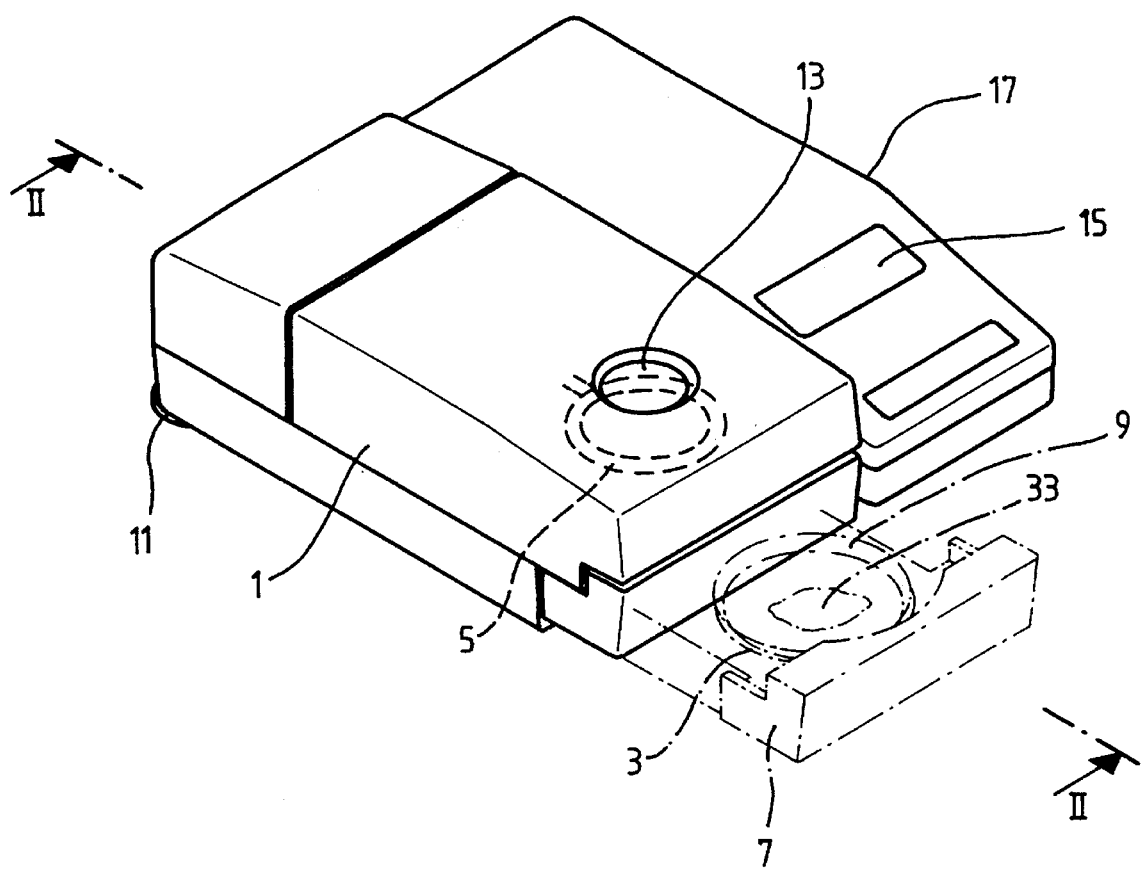
FIG. 1 is a perspective view of a dryer with precision balance according to the present invention.

A balance 3 and a heat source 5 are mounted in a housing 1 of a drying apparatus. The balance 3 is mounted on a component 7 which is movable relative to the housing 1. For charging the weighing dish 9, the balance 3 can be moved out of the housing 1 and, for carrying out the thermal treatment, the balance 3 can be moved into the housing 1. The housing 1 has legs 11 and may include at the top thereof an inspection glass 13 for observing material 33 to be weighed during the drying process. In addition, display instruments 15 are provided which may be accommodated in a display block 17 arranged next to the housing 1. Alternatively, the display elements 15 may also be provided directly on the housing 1 of the drying apparatus. A dryer of this type is disclosed, for example, in the above-mentioned pending application Ser. No. 08/163,925, now U.S. Pat. No. 5,485,684.

Figure 2:
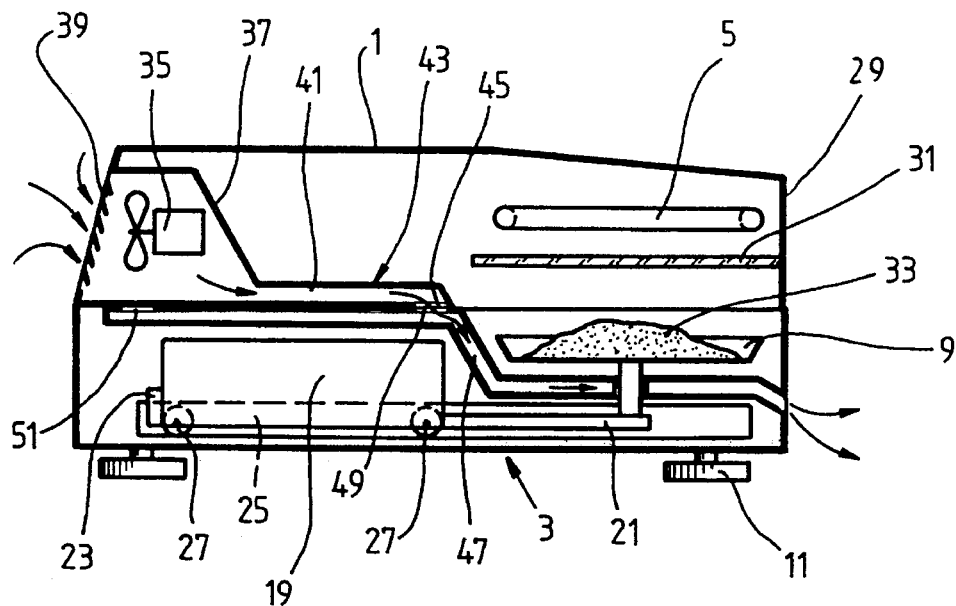
FIG. 2 is a cross-sectional view of the dryer taken along sectional line II—II of FIG. 1, with the balance being shown in the moved-in position.
Figure 3:
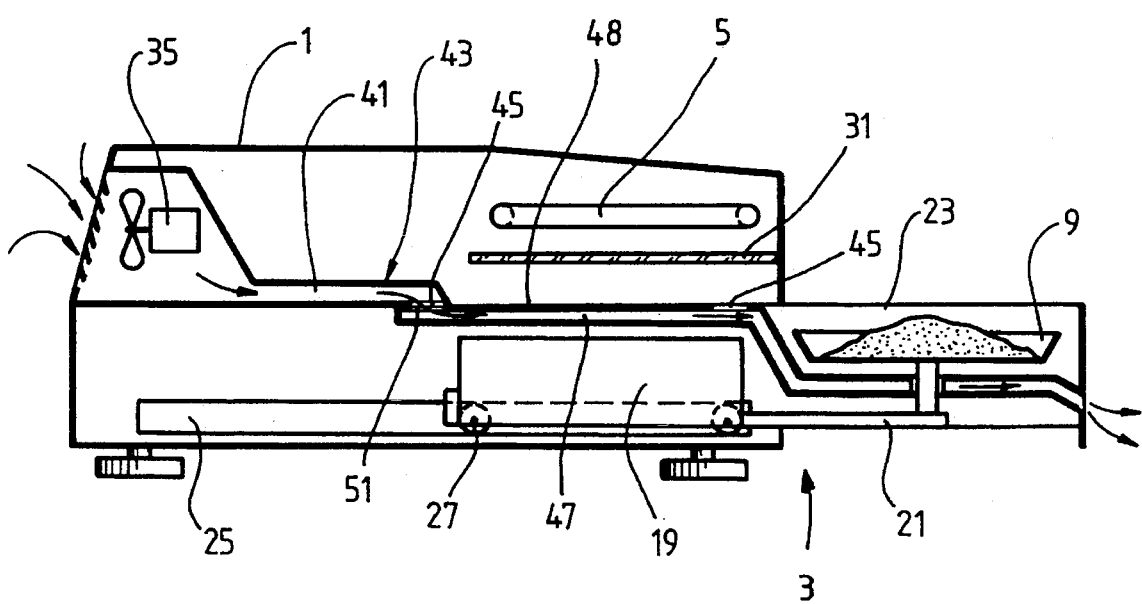
FIG. 3 is a cross-sectional view of the dryer taken along sectional line II—II of FIG. 1, with the balance being shown in the moved-out position.

In accordance with a first embodiment of the present invention illustrated in FIGS. 2 and 3, reference numeral 19 denotes the measuring cell of the balance 3, wherein the measuring cell is schematically illustrated as a rectangle. The measuring cell 19 is placed on a load-receiving unit 21 which protrudes at the front side beyond the measuring cell 19. The balance 3 is mounted on a drawer-like pull-out member 23. The pull-out member 23 can be moved horizontally in and out of the housing 1 by means of rails 25 mounted in the housing 1 and rollers 27 guided in the rails 25. The pull-out member 23 is mounted in the lower half of the housing 1. The measuring cell 19 is mounted in the rear portion of the pull-out member 23 and the weighing dish 9, supported by the load-receiving unit 21, is arranged in the front portion of the pull-out member 23. When the pull-out member 23 is in the moved-in position, the weighing dish 9 is located underneath a heat source 5, for example, a ring-shaped infrared heating rod. A protective glass 31 may be mounted underneath the heat source 5 for protecting the heat source 5 against vapors or portions of the material 33 to be weighed which may splatter from the weighing dish 9.

A blower 35 is mounted in the rear portion of the housing 1 in a suction chamber 37. The blower 35 is constructed and intended to take in ambient air through a suction opening 39 in the rear wall of the housing 1. The suction chamber 37 is connected to a first section 41 of a duct 43. The first section 41 of the duct 43 is arranged fixed to the housing and has an outlet opening 45 at its bottom side and at the end facing the front side 29 of the housing 1. The end face of the section 41 is closed. The first section 41 has an essentially rectangular cross-section and extends laterally at least over the entire width of the measuring cell 19 which is, arranged underneath the first section 41 when the measuring cell 19 is in the moved-in position.

The second section 47 of the duct 43 is mounted on the pull-out member 23. The second section 47 also has an essentially rectangular cross-section, wherein the width of the second section 47 preferably corresponds to the width of the first section 41. The second section 47 extends over the measuring cell 19 and, from the measuring cell 19, under the weighing dish 9 to the front side 29 of the housing 1. The top side and the bottom side of the second section 47 are arranged at a distance from the measuring cell 19 as well as from the weighing dish 9 and from the load-receiving unit 21. The top side of the second section 47 which rests against the bottom side of the first section 41 has in the area of the measuring cell 19 two openings 49 and 51. In the moved-in position of balance 3, the first opening 49 is located opposite the outlet opening 45 of the first section 41. The second opening 51 is located at the rearward end of the second section 47 and is located opposite the outlet opening 45 in the first section 41 when the drawer-like pull-out member 23 is in the moved-out position shown in FIG. 3. When the balance is in the moved-in position, the second opening 51 is closed by the bottom wall of the section 41.

The two sections 41 and 47 of the duct 43 make it possible to conduct air through the duct 43 when the balance 3 is in the moved-in position, i.e., during the drying process, as well as when the pull-out member 23 is in the moved-out position for charging the weighing dish 9. In the latter position, the measuring cell 19 is located directly under the heat source 5 which, although already switched off, still radiates residual heat. In addition, residual heat is released downwardly by the protective glass 31. The air flowing through the duct 43 forms a thermal insulation and additionally cools the surface of the second section 47 of the duct 43 which has been heated by the heat source 5. The air conducted through the duct 43 leaves the duct 43 at the front side 29 of the housing 1. The surface 48 of the section 47 is preferably polished to act as a mirror for heat reflection. This makes it possible to monitor the cooling process easily and at any time.

Figure 4:
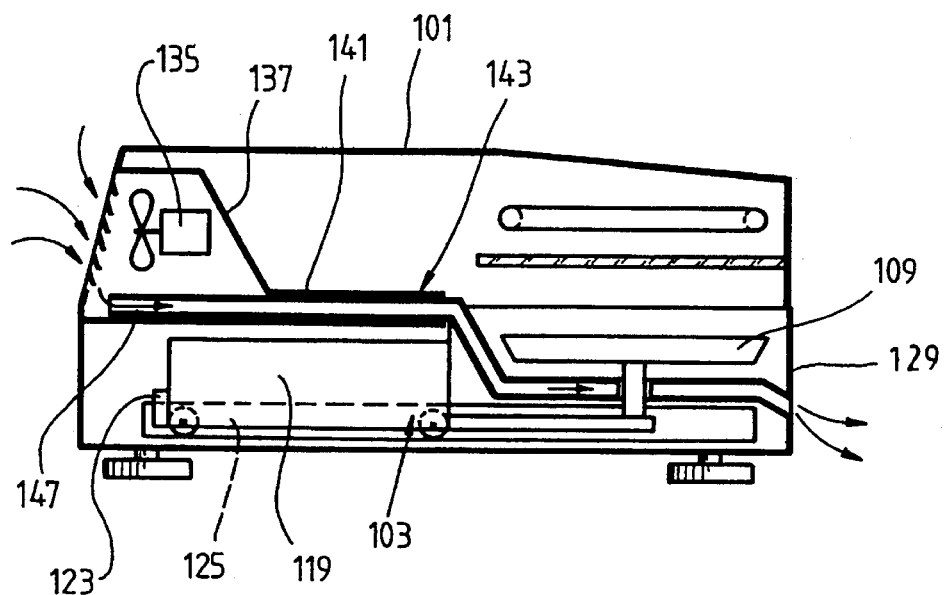
FIG. 4 is a cross-sectional view of another embodiment of the dryer according to the present invention, with the balance being shown in the moved-in position.
Figure 5:
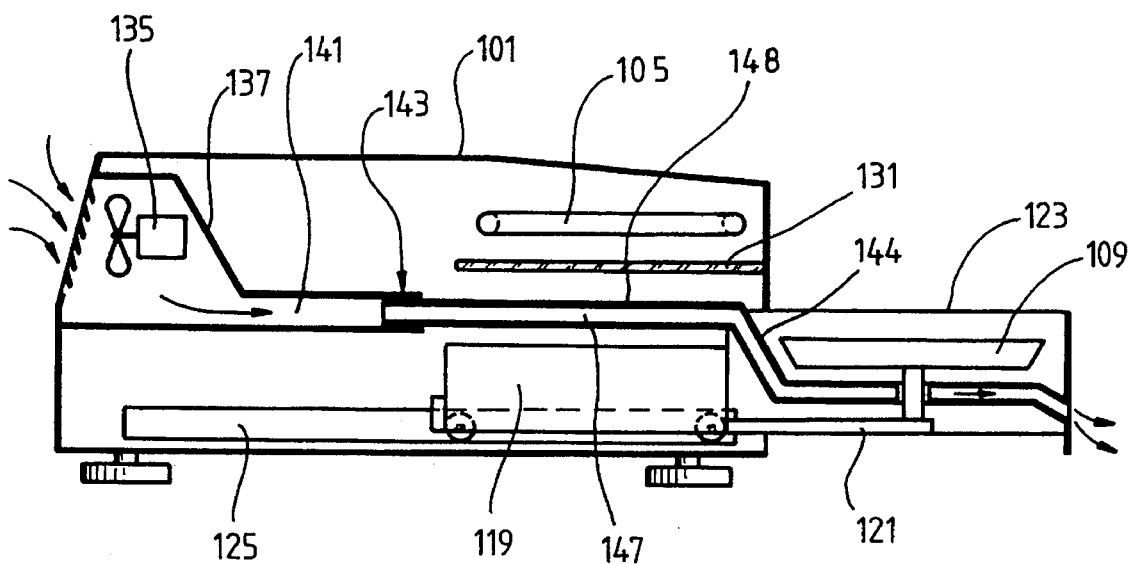
FIG. 5 is cross-sectional view of the embodiment of FIG. 4, with the balance shown in the moved-out position.

In the second embodiment of the present invention shown in FIGS. 4 and 5, a measuring cell 119 with a weighing dish 109 mounted on a load-receiving unit 121 are mounted in a housing 101. The balance 103 is mounted in a pull-out member 123 which is mounted on rails 125 so as to be movable in and out of the housing 101. Analogous to the first embodiment, a blower 135 is mounted in a suction chamber 137. On the pressure side, the suction chamber 137 is in communication with a first section 141 of a duct 143 whose cross-section is essentially rectangular and which extends at least over the entire width of the measuring cell 119 located therebelow. The pressure end of the first section 141 forms a vertically arranged opening.

A second section 147 of the duct 143 extends over the measuring cell 119 and then through a downwardly inclined intermediate section 144 underneath the weighing dish 109 and to the forward end of the pull-out member 123. The second section 147 is always located at a distance from the measuring cell 119 as well as from the weighing dish 109. In contrast to the first embodiment, the two sections 141 and 147 are not located one above the other; rather, the second section 147 slides telescopically within the first section 141.

During drying, i.e., when the balance 103 is moved into the housing 101, the second section 147 of the duct 143 is inserted deeply into the first section 141. The air taken in by the blower 145 is conducted from the suction chamber 137 essentially directly into the second section 147 and is conducted through the second section 147 over the measuring cell 119 and under the weighing dish 109 to the front side 129 of the housing 1. During charging of the weighing dish 109 when the measuring cell is located underneath the heat source 105 and the protective glass 131, a continuous air flow is ensured because the air taken in by the blower 135 is initially blown into the first section 141 and is conducted from the first section 141 to the second section 147 which is always above the measuring cell 119 and protects the measuring cell 119 against the influence of heat.

By selecting suitable tolerances of the first and second sections 141, 147 or by using appropriate sealing means, not shown, an air transport is ensured which is essentially free of losses.

The surface 148 of the upper wall of the section 147 is preferably polished to act as a mirror for heat reflection.

Of course, it would alternatively also be possible to guide the first section 141 within the second section 147.

Figure 6:
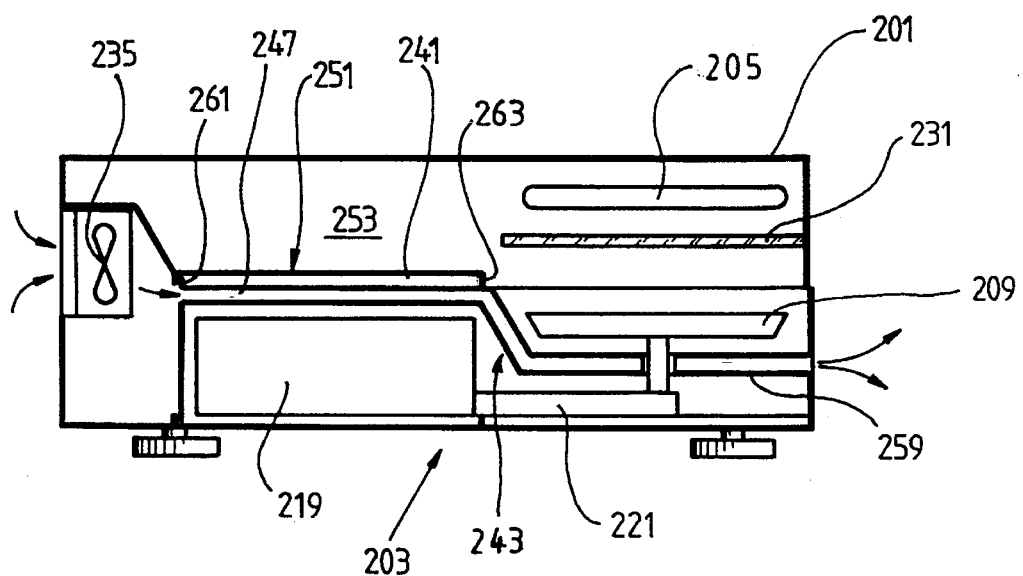
FIG. 6 is a cross-sectional view of a third embodiment of the dryer according to the present invention, with the balance being shown in the moved-in position.
Figure 7:
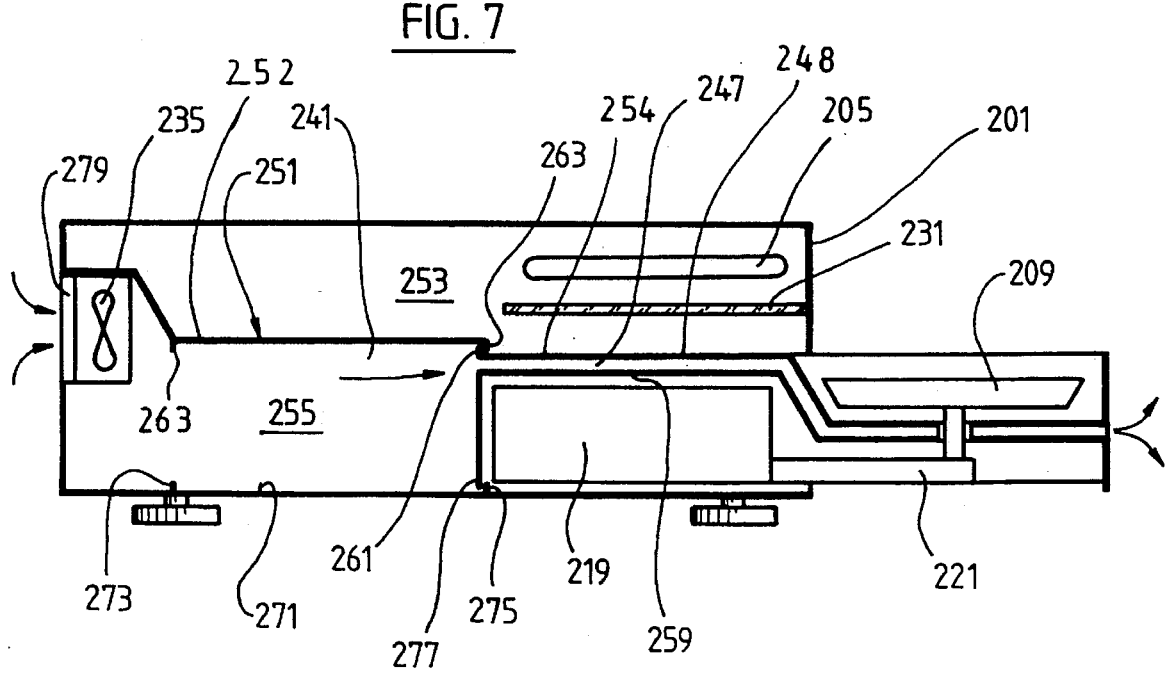
FIG. 7 is a cross-sectional view of the third embodiment of the dryer, with the balance shown in the moved-out position.

In the third embodiment of the invention according to FIG. 6 and 7, the measuring cell 219 with the weighing dish 209 mounted on the load-receiving unit 221 are mounted in the housing 201. As in the two previous embodiments, the balance 203 is mounted so as to be movable into and out of the housing 201.

A blower 235 is mounted in the area of the rear wall of the housing 201. The blower 235 takes in ambient air into the interior of the housing 201 which is divided by a wall 251 into a hot portion 253 and a cold portion 255. The wall 251 is composed of two parts, wherein the rearwardly located first part 252 is stationary and connected to the housing 201. The forward second part 254 is fastened to the balance 203 and is movable together with the balance 203 relative to the housing 201. A cover 259 is fastened to the balance 203 underneath the second part 254 and at a distance from the second part 254. The cover 259 covers the load-receiving unit 221 and the measuring cell 219. The second part 254 and the cover 259 are connected to each other along their side edges and form the duct section 247. The duct section 247 has a reflecting surface 248. The duct section 247 ends and is open at the end face of the housing 201 of the dryer. The duct section 247 is also open at its inlet side and is in communication with the blower 235. The cold portion 255 underneath the first part 252 forms the duct section 241 when the balance is moved out.

When the balance 203 is in the moved-in position as shown in FIG. 6, the second section 247 is located underneath the first section 241 and, in this position of the balance 203, the first section 241 forms a dead space: A first sealing lip 261 on the second section 247 and a second sealing lip 263 each at the beginning and the end of the first section 241 prevent the passage of air between the two wall parts 252 and 254 which are located one above the other.

On the bottom 271 of the housing 201 are provided a first web 273 and a second web 275 extending transversely of the direction of movement of the balance 203, wherein the lower edge 277 of the cover 259 comes alternatingly into contact with the webs 273 and 275 when the balance 203 is moved in and moved out.

The air taken in by the blower 235 and possibly cleaned by a filter 279 flows into the interior of the housing 201 and from there between the wall 251 and the cover 259 toward the outside. The air removes the heat radiated by the heat source 205 and the protective glass 231 toward the second wall part 254.

In all embodiments with motor drives of the balance, a circuit may additionally be provided which serves to automatically pull the moved-out balance back into the housing after a waiting period. This makes it possible to reduce unnecessary dwell time of the weighing cell underneath the heat source.

While specific embodiments of the invention have been shown and described in detail to illustrate the inventive principles, it will be understood that the invention may be embodied otherwise without departing from such principles.

We claim:

1. A dryer mounted in a housing, the dryer comprising a heat source for producing heat radiation, a precision balance comprising a weighing dish and a measuring cell, a load-receiving unit supporting the weighing dish and mounted on the measuring cell, the precision balance being configured for determining the moisture content of a material to be weighed placed on the weighing dish and subjected to the heat radiation of the heat source and comprising means for moving the precision balance into and out of the housing for making the material accessible, further comprising a duct for conducting an air flow between the weighing dish and the load-receiving unit, the duct being circumferentially closed and extending above the measuring cell and below the weighing disk without contacting the measuring cell and the weighing dish.

2. The dryer according to claim 1, wherein the housing has a front side and a rear side, the duct extending from the rear side to the front side of the housing.

3. The dryer according to claim 2, wherein the duct has a rectangular cross-section, the measuring cell having a width, the duct extending over the entire width of the measuring cell.

4. The dryer according to claim 2, wherein the duct comprises a rear section and a front section, wherein the rear section and the front section are connected to one another.

5. The dryer according to claim 4, wherein the rear section of the duct is attached to the housing, the rear section of the duct having an input opening at the rear side of the housing, further comprising a blower mounted at the input opening, wherein the front section of the duct is mounted on the balance.

6. The dryer according to claim 4, wherein the front section and the rear section of the duct are constructed so as to slide telescopically into one another.

7. The dryer according to claim 4, wherein the rear and front sections of the duct are located partially one above the other, the rear and front sections each having walls contacting one another, wherein the wall of the rear section defines an opening and the wall of the front section defines first and second openings, wherein the opening of the rear section is in communication with the first opening of the front section when the balance is in a moved-in position and the opening of the rear section is in communication with the second opening of the front section when the balance is in a moved-out position.

8. The dryer according to claim 4, wherein the front section of the duct has an upper wall surface, the wall surface being polished for providing a mirror surface for heat reflection.

* * * * *